United States Patent [19]

Engel et al.

[11] 4,263,308
[45] Apr. 21, 1981

[54] N-ALKOXY-DITHIENYLPIPERIDINES, PHARMACEUTICAL COMPOSITIONS THEREOF AND METHODS OF USE THEREOF

[75] Inventors: Jurgen Engel, Alzenau; Axel Kleemann, Hanau; Ute-Achterrath Tuckermann, Neu-Isenburg; Klaus Thiemer, Hanau, all of Fed. Rep. of Germany

[73] Assignee: Degussa Aktiengesellschaft, Frankfurt, Fed. Rep. of Germany

[21] Appl. No.: 112,100

[22] Filed: Jan. 14, 1980

[30] Foreign Application Priority Data

Jan. 17, 1979 [GB] United Kingdom ............... 1660/79

[51] Int. Cl.³ ................. C07D 417/14; A61K 31/445
[52] U.S. Cl. ..................................... 424/267; 546/212; 546/213
[58] Field of Search ................. 546/212, 213; 424/267

[56] References Cited

U.S. PATENT DOCUMENTS

| 2,739,968 | 3/1956 | Sperber et al. ................. 546/212 |
| 4,175,088 | 11/1979 | Kleemann et al. ................. 549/59 |

FOREIGN PATENT DOCUMENTS

| 2016667 | 10/1970 | Fed. Rep. of Germany ........... 542/432 |
| 2800536 | 7/1978 | Fed. Rep. of Germany ............. 546/59 |

Primary Examiner—Robert T. Bond
Attorney, Agent, or Firm—Cushman, Darby & Cushman

[57] ABSTRACT

There are prepared compounds of the formula

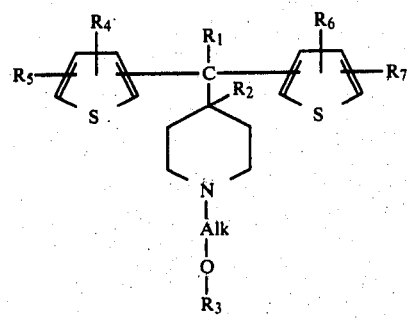

where $R_1$ is hydrogen or hydroxy, $R_2$ is hydrogen or $R_1$ and $R_2$ together represent a second bond between the carbon atoms carrying $R_1$ and $R_2$, Alk is a $C_2$–$C_6$ alkylene group, $R_3$ is a $C_3$–$C_8$-cycloalkyl group, a $C_1$–$C_6$-alkyl group, a $C_1$–$C_6$-hydroxyalkyl group or a $C_2$–$C_6$-hydroxyalkoxy-$C_1$–$C_6$-alkyl group and the groups $R_4$, $R_5$, $R_6$ and $R_7$ are the same or different and are hydrogen, $C_1$–$C_6$-alkyl group or halogen atoms, their N-oxides, their quaternary salts and their acid addition salts. There are also described processes for their production. The compounds have a strong bronchospasmolytic activity, antianaphylactic activity and an antihistamine-antiserotonine activity.

30 Claims, No Drawings

N-ALKOXY-DITHIENYLPIPERIDINES, PHARMACEUTICAL COMPOSITIONS THEREOF AND METHODS OF USE THEREOF

BACKGROUND OF THE INVENTION

Through Sperber U.S. Pat. No. 2,739,968 there are known compounds having spasmolytic, analgesic and antihistamine activity having the following formula

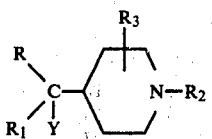

wherein for example $R_2$ is a methyl or an ethyl group, R and $R_1$ are two thienyl-(2) groups, $R_3$ is hydrogen and Y is hydrogen or a hydroxy group or also together with the piperidine ring can form a double bond.

The German Auslegeschrift 2016667 is directed to 4-(diphenyl-methylene)-piperidines of the general formula

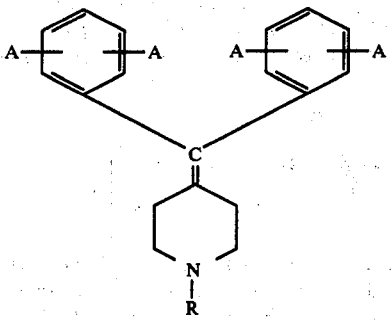

in which A in each case is the same or different and is a hydrogen or halogen atom, a trifluoromethyl group or an optionally branched alkyl or alkoxy group with 1 to 4 carbon atoms and R is an optionally branched hydroxyalkyl, hydroxyalkoxyalkyl or hydroxyalkoxyalkoxyalkyl group wherein the alkyl and alkoxy groups again in each case have 1 to 4 carbon atoms with broncholytic vasodilatory, coronary dilatory and antihistamine activity.

SUMMARY OF THE INVENTION

There are prepared compounds of the formula I

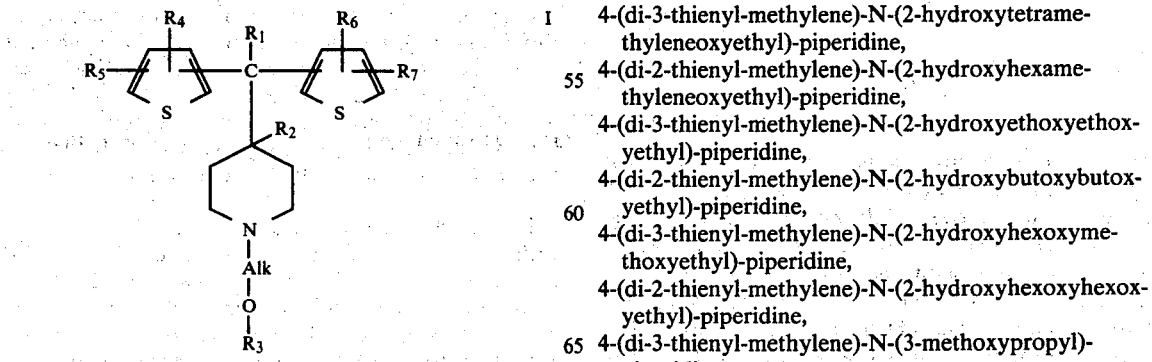

where $R_1$ is hydrogen or hydroxy, $R_2$ is hydrogen or $R_1$ and $R_2$ together represent a second bond between the carbon atoms carrying $R_1$ and $R_2$, Alk is a $C_2-C_6$ alkylene group, $R_3$ is a $C_3-C_8$-cycloalkyl group, a $C_1-C_6$ alkyl group, a $C_1-C_6$ hydroxyalkyl group or a $C_2-C_6$-hydroxyalkoxy $—C_1-C_6$-alkyl group and the groups $R_4$, $R_5$, $R_6$ and $R_7$ are the same or different and are hydrogen, $C_1-C_6$-alkyl group or halogen atoms, their N-oxides, their quaternary salts and their acid addition salts.

The alkyl groups and alkylene chain Alk can be straight or branched chain. In case $R_4$, $R_5$, $R_6$ and/or $R_7$ are alkyl these particularly have 1 to 4 carbon atoms, preferably they are methyl. In case $R_4$, $R_5$, $R_6$ and/or $R_7$ are halogen they are for example fluorine, chlorine or bromine. Alk signifies an alkylene group as for example the ethylene, trimethylene, tetramethylene, pentamethylene or hexamethylene group, especially the Alk group consists of two or three carbon atoms. In case the residue $R_3$ is a hydroxyalkyl group or hydroxyalkoxyalkyl group, the alkyl portion especially consists of 1 to 4 carbon atoms, preferably 2 carbon atoms. In case $R_3$ is the hydroxyalkoxyalkyl group the alkoxy portion for example consists of 2 to 4 carbon atoms.

In addition to the compounds mentioned in the specific examples illustrative of other novel compounds within the invention and which can be used for pharmaceutical purposes within the invention include 4-(di-3-thienyl-methylene)-N-(2-ethoxyethyl)-piperidine, 4-(di-3-thienyl-methylene)-N-(2-propoxy-ethyl)-piperidine, 4-(di-2-thienyl-methylene)-N-(2-butoxyethyl)-piperidine, 4-(di-2-thienyl-methylene)-N-(2-isopropoxyethyl)-piperidine, 4-(di-3-thienyl-methylene)-N-(2-sec.butoxyethyl)-piperidine, 4-(di-2-thienyl-methylene)-N-(2-hexoxyethyl)-piperidine, 4-(di-3-thienyl-methylene)-N-(2-cyclooctoxyethyl)-piperidine, 4-(di-30thienyl-methylene)-N-(2-cyclohexoxyethyl)-piperidine, 4-(di-2-thienyl-methylene)-N-(2-cyclopropoxyethyl)-piperidine, 4-(di-3-thienyl-methylene)-N-(2-hydroxymethoxyethyl)-piperidine, 4-(di-2-thienyl-methylene)-N-(2-hydroxypropoxyethyl)-piperidine, 4-(di-3-thienyl-methylene)-N-(2-hydroxytrimethyleneoxyethyl)-piperidine, 4-(di-3-thienyl-methylene)-N-(2-hydroxytetramethyleneoxyethyl)-piperidine, 4-(di-2-thienyl-methylene)-N-(2-hydroxyhexamethyleneoxyethyl)-piperidine, 4-(di-3-thienyl-methylene)-N-(2-hydroxyethoxyethoxyethyl)-piperidine, 4-(di-2-thienyl-methylene)-N-(2-hydroxybutoxybutoxyethyl)-piperidine, 4-(di-3-thienyl-methylene)-N-(2-hydroxyhexoxymethoxyethyl)-piperidine, 4-(di-2-thienyl-methylene)-N-(2-hydroxyhexoxyhexoxyethyl)-piperidine, 4-(di-3-thienyl-methylene)-N-(3-methoxypropyl)-piperidine, 4-(di-3-thienyl-methylene)-N-(4-methoxybutyl)-piperidine, 4-(di-2-thienyl-methylene)-N-(2-methoxypropyl)-piperidine,
4-(di-2-thienyl-methylene)-N-(6-methoxyhexyl)-piperidine,
4-(di-3-thienyl)-(N-methoxyethyl-4-piperidyl)-carbinol,
4-(di-3-thienyl)-(N-hydroxyethoxyethyl-4-piperidyl)-carbinol,
4-(di-2-thienyl)-(N-butoxyethyl-4-piperidyl)-carbinol,
4-(di-3-thienyl-methyl)-N-(2-methoxyethyl)-piperidine,
4-[3-thienyl-(2,5-dimethyl-3-thienyl)-methylene]-N-(2-methoxyethyl)-piperidine,
4-[di-3-(2,5-dimethyl)-thienyl-methylene]-N-(2-ethoxyethyl)-piperidine,
4-[di-2-(3,5-dibutyl)-thienyl-methylene]-N-(2-methoxyethyl)-piperidine,
4-[3-thienyl-(2,5-dihexyl-3-thienyl)-methylene]-N-(2-methoxyethyl)-piperidine,
4-[3-thienyl-(2-methyl-3-thienyl)-methylene]-N-(2-methoxypropyl)-piperidine,
4-[2-thienyl-(2.5-dichloro-3-thienyl)-methylene]-N-(2-methoxyethyl)-piperidine,
4-[2-thienyl-(2-chloro-3-thienyl)-methylene]-N-(2-methoxyethyl)-piperidine,
4-[di-3-(2,5-dichloro)-thienyl-methylene]-N-(3-methoxypropyl)-piperidine,
4-[di-3-(2-bromo)-thienyl-methylene]-N-(2-methoxyethyl)-piperidine,
4-[di-3-(2-fluoro)-thienyl-methylene]-N-(2-hydroxyethoxyethyl)-piperidine,
4-[di-3-thienyl-methylene]-N-(2-methoxyethyl)-piperidine oxide,
4-[di-3-thienyl-methylene]-N-methyl-(2-methoxyethyl)-piperidinium iodide.

The compounds of the invention are pharmacodynamically active and have a strong branchospasmolytic activity, additionally an antihistamine-antiserotonine activity, as well as an antianaphylactic activity (asthma prophylactic activity). An object of the invention thus is to make available compounds with favorable pharmacodynamic properties which are useful as medicines.

The compounds of the present invention of Formula I are prepared by either (a) in a compound of the formula

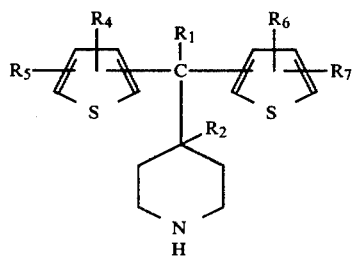

or an N-metal derivative thereof (e.g. where the metal is sodium or lithium) and where $R_1$, $R_2$, $R_3$, $R_4$, $R_5$, $R_6$ and $R_7$ are as defined above and the piperidine ring can also contain three conjugated double bonds, introducing by alkylation at the N-atom the group —Alk—O—$R_3$ in one or two steps wherein $R_3$ is as defined above and treating the compounds obtained in a given case with a reducing agent and/or dehydrating agent and/or converting the compound into the N-oxide; or (b) reacting a compound of the formula:

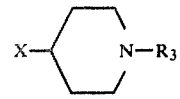

which also can contain three conjugated ring double bonds where $R_3$ is as defined above ($R_3$ is eliminated in case a pyridine ring is present) and X stands for either (A) the group —COZ where Z is a halogen atom, e.g. chlorine, bromine, or iodine, or a $C_1$–$C_6$-alkoxy group, e.g. methoxy, ethoxy, propoxy, butoxy or hexoxy or a thienyl group which in a given case is substituted once or twice by halogen atoms and/or $C_1$–$C_6$ alkyl groups or (B) lithium or the group —MgHal where Hal is chlorine, bromine or iodine, or in the case of (A) with a compound

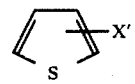

wherein X' is lithium or the group —MgHal and the thienyl group also can be substituted once or twice by halogen atoms and/or $C_1$–$C_6$-alkyl groups or in the case of (B) is reacted with a compound of the formula

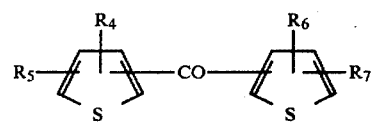

and the compounds obtained in a given case treated with a reducing agent and/or dehydrating agent and/or alkylated through the group —Alk—O—$R_3$ and/or converted into the N-oxide.

Process (a)

The alkylation of compounds of Formula II is carried out by reacting the compound of Formula II with a compound of the formula

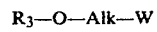

wherein $R_3$ and Alk are as defined above and W is a halogen atom such as chlorine, bromine or iodine or the group $R_8SO_2O$— where $R_8$ is a $C_1$–$C_6$ alkyl group, phenyl or naphthyl or phenyl or naphthyl substituted with one or more lower alkyl groups, e.g., methyl, ethyl, propyl, such as a tosyl group. This alkylation can also be undertaken in two steps in which the compound of formula II is first reacted with a compound HO—Alk—W wherein W can also form an ethylene oxide ring with the hydroxy group in case this is adjacent, and the reaction product subsequently reacted with a compound $R_3$—W wherein W has the meaning set forth above.

This alkylation reaction can be carried out with or without a solvent at a temperature between 20° and 200° C., preferably 50° to 150° C. As solvents or dispersing agent there can be used for example aromatic hydrocarbons such as for example benzene, toluene or xylene; aliphatic ketones as for example acetone or methyl ethyl ketone; halogenated hydrocarbon as for example chloroform, carbon tetrachloride, chlorobenzene or methylene chloride; aliphatic ethers as for example dibutyl ether; cyclic ethers as for example tetrahydrofurane or dioxane; sulfoxides as for example dimethyl sulfoxide; tertiary acid amides as for example dimethyl formamide or N-methyl pyrrolidone; aliphatic alcohols such as methanol, ethanol, isopropanol, amyl alcohol or tert. butanol; cycloaliphatic hydrocarbons such as cyclohexane and the like. There can also be used aqueous mixtures of the solvents mentioned. Frequently the process is operated at the reflux temperature of the solvent or dispersing agent used. Generally the alkylation reactants are added in excess. In a given case the reaction can also take place in the presence of acid binding agents such as alkali carbonates (potash or sodium carbonate), alkali hydroxides (e.g. sodium hydroxide or potassium hydroxide) or tert. amines (for example triethyl amine). The latter is especially true if the corresponding halides are employed.

The compound of formula II can also for example be employed in the form of a metal salt, especially an alkali salt (sodium or potassium salt for example). This is especially true if the other reactant is a halide.

In carrying out the reaction as the ethylene oxide starting material in place of the ethyleneoxy compounds there can also be employed the corresponding halohydrin or a mixture of both of these compounds (crude-synthesis product).

Starting compounds of formula II can be obtained by the process or Engel application Ser. No. 112,099 filed Jan. 14, 1980, corresponding to British priority application 7,901,659 filed Jan. 17, 1979. The entire disclosure of the Engel application and the corresponding British application are hereby incorporated by reference and relied upon. A certified copy of British Application 7,901,659, filed Jan. 17, 1979 is a part of the record in Engel Application Ser. No. 112,099, filed Jan. 14, 1980 and the certified copy was filed along with the original application papers in Ser. No. 112,099.

The splitting off of water from compounds of formula I wherein $R_1$ is the hydroxy group and $R_2$ is hydrogen (the remaining symbols can have the stated meanings) is carried out suitably at higher temperatures, for example in a temperature range of 20°-150° C. Preferably there are used solvents as for example glacial acetic acid, benzene, dioxane, lower aliphatic alcohols, e.g. methyl alcohol, ethyl alcohol, propyl alcohol, isopropyl alcohol.

As agents for splitting off water there can be used for example mineral acids such as sulfuric acid or hydrohalic acids, e.g. hydrochloric acid or hydrobromic acid; organic acids such as oxalic acid, formic acid, thionyl chloride; zinc chloride, tin chloride; boron trifluoride; potassium hydrogen sulfate; aluminum chloride; phosphorus pentoxide; aluminum oxide; acid chlorides, e.g. acetyl chloride; red phosphorus plus iodine in the presence of water.

Frequently a partial splitting off of water takes place already in the working up of the reaction products obtained through reaction of compounds of formula III with compounds of formula IV or V.

The reduction of compounds of formula I wherein $R_1$ and $R_2$ form the double bond or $R_1$ is the hydroxy group and $R_2$ is hydrogen as well as the products of the process which contain three double bonds in the piperidine ring (the remaining symbols having the stated meaning) can be carried out for example with hydrogen in the presence of hydrogenation catalysts, suitably in a solvent such as an alcohol, e.g. isopropyl alcohol, ethyl alcohol or methyl alcohol, dioxane, tetrahydrofurane, benzene, acetic acid, ethyl acetate, etc. As hydrogenation catalyst there are particularly employed noble metal catalysts such as palladium, platinum, etc. or sulfidic catalysts such as palladium sulfide, platinum sulfide, rhenium heptasulfide and the like. The catalysts can be used with or without carrier. As carriers there are suited for example barium sulfate, aluminum oxide, etc. The hydrogenation is suitably carried out at a temperature between 20° and 100° C. at normal pressure or elevated pressure up to for example 100 bar. A pressure between 2 and 20 bar is preferred.

Furthermore there can be used as reducing agent nasant hydrogen, for example metallic sodium in a lower alcohol (ethanol for example), with or without addition of water, sodium in liquid ammonia, sodium amalgam in the presence of an acid such as dilute hydrochloric acid, dilute sulfuric acid or acetic acid. In this case there is generally employed room temperature or elevated temperature up to about 150° C.

Furthermore, for example it is also possible to employ electrolytic reduction or reduction with other hydrogen supplying agents such as complex metal hydrides, for example alkali-borohydrides, e.g. sodium borohydride, lithium alanate, sodium-bis-(2-methoxy-ethoxy)-aluminum hydride in the presence of hydrogenation catalysts.

In the reduction, especially with catalytic hydrogenation ($Pd-CaCO_3$) or also electrolytic reduction, in a given case there can be removed halogen atoms in the 2,5-positions on the thiophene ring. A selective splitting off of halogen atoms in the thiophene ring is possible for example with zinc/glacial acetic acid.

If there are present as starting materials compounds of formula I wherein $R_1$ is the hydroxy group and $R_2$ is hydrogen then there is frequently recommended the simultaneous addition of dehydrating materials. As dehydrating agent there can be used for example mineral acids such as sulfuric acid or hydrohalic acids, e.g. hydrochloric acid or hydrobromic acid, organic acids such as oxalic acid or formic acid; thionyl chloride; aluminum chloride; zinc chloride, tin chloride, boron trifluoride, potassium hydrogen sulfate; aluminum oxide; phosphorus pentoxide; acid chlorides, e.g. acetyl chloride or benzoyl chloride. Especially there is used as the reducing agent nascent hydrogen in acid medium.

The reduction can be carried out in solution or suspension. As solvents there can be employed for example those already mentioned.

In case the product of the process contains three conjugated double bonds in the piperidine ring (pyridine ring) above all there are considered for the hydrogenation of the nucleus of this pyridine ring platinum, rhodium and ruthenium catalysts ($PtO_2$; rhodium/carbon, ruthenium dioxide) at a temperature between 20° and 50° C. and normal pressure to 10 bar. As solvents there are suited for this particularly lower alcohols, e.g., methanol, ethanol or isopropanol, dioxane, tetrahydrofurane, glacial acetic acid, alcoholic hydrochloric acid. Frequently it is suitable to hydrogenate the corresponding hydrochloride. A hydrogenation of the pyridine ring, however, for example is also possible with alkali metals (e.g. sodium) in lower alcohols (e.g. ethanol) at 20° to 150° C.

The conversion of the compound of formula I into the corresponding N-oxide can be carried out for example in inert solvents such as chloroform or other chlorohydrocarbons, benzene, toluene, acetone or ethyl acetate with hydrogen peroxide, a conventional aliphatic or aromatic peracid (peracetic acid, perbenzoic acid, m-chloroperbenzoic acid) or other mono substitution products of hydrogen peroxide such as alkyl peroxides (for example tert. butyl peroxide) at a temperature between 0° and 150° C., preferably 0° to 100° C.

Process (b)

This process is suitably carried out in a temperature range between −100 and +150° C., preferably −75° to +100° C. or up to +50° C. In case there is used a thienyl (3)-metal compound (especially thienyl lithium) or a thienyl-(3)-Grignard compound there are preferably employed low temperatures, especially below −50° C. in an inert medium. In such cases it is advantageous to carry out the reaction at temperatures between −70° and −80° C. The temperature between −70° and −80° C. is especially suitable for thienyl-(3)-metal compounds. As solvents there are suitable for example saturated aliphatic symmetrical and unsymmetrical dialkyl ethers with alkyl groups of for example of 1–6 carbon atoms, dimethyl ether, diethyl ether, dipropyl ether, diisopropyl ether, propyl butyl ether, dibutyl ether or dihexyl ether, $C_1$–$C_6$-alkyl ethers of cycloalkanols and alkyl substituted cycloalkanols wherein the cycloalkanol ring in each case has 3,4,5 or 6 carbon atoms, e.g. methyl cyclohexyl ether, methyl cyclopentyl ether or ethyl cyclohexyl ether; saturated $C_5$–$C_9$ aliphatic or $C_3$–$C_7$-cycloaliphatic hydrocarbons wherein the latter preferably can be substituted one to three times by $C_1$–$C_4$ alkyl groups, e.g. hexane, pentane, octane, nonane, cyclohexane, cyclopentane, cycloheptane, methyl cyclohexane, methyl cyclopentane, ethyl cyclohexane, butyl cyclohexane, dimethyl cyclohexane or trimethyl cyclohexane; tetrahydrofurane, benzene, benzene substituted by $C_1$–$C_3$-alkyl groups, e.g. toluene, xylene, ethyl benzene or propyl benzene. Especially preferred are ethers and aliphatic or cycloaliphatic hydrocarbons which are liquid in the range between −80° and +20° C.

The stated solvents can also be used in mixtures. For example a solvent mixture can be used which consists of a saturated ether and benzene substituted by $C_1$–$C_3$-alkyl groups. These kinds of solvent mixtures are described for example in German Offenlegungsschrift 2,800,536 and related Kleemann U.S. Pat. No. 4,175,088, the entire disclosure of which is hereby incorporated by reference and relied upon.

A corresponding excess of metal organic compound is always necessary if the other reactants contain active hydrogen (amino-, hydroxy groups, salt). However, it is frequently recommended to use an excess of metal organic compound since better yields are produced through this.

In case Z in the group —COZ (formula III is a halogen atom it is preferably chlorine, bromine or iodine.

Compounds of formula I wherein $R_1$ is the hydroxy group and $R_2$ is hydrogen and the remaining symbols are as defined can be converted into compounds of formula I by treatment with a dehydrating agent, wherein $R_1$ and $R_2$ together form a second bond between the carbon atoms carrying the substituents $R_1$ and $R_2$. This dehydration takes place in the manner already given above.

Compounds of formula I wherein $R_1$ and $R_2$ form the second bond between the carbon atoms carrying the substituents $R_1$ and $R_2$ or wherein $R_1$ is the hydroxy group and $R_2$ is hydrogen and the remaining symbols are as set forth above can be converted into compounds in which $R_1$ and $R_2$ are hydrogen by treatment with reducing agents. Conditions for this reduction have already been given above.

The conversion into the N-oxide likewise takes place as already stated above.

Starting materials of the formula

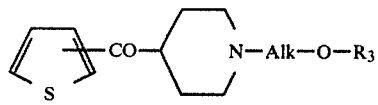

wherein the thienyl group also can be substituted by halogen or lower alkyl groups can be obtained for example through reaction of the corresponding thienyl lithium or thienyl Grignard compound with the compound

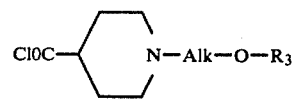

or through reaction of the corresponding thienyl cyanide or thienyl carbonyl chloride with the compound

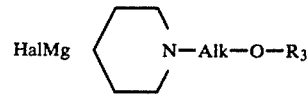

(Hal = Chlorine or Bromine)

in a solvent or suspension agent as is customary for Grignard reactions (for example lower saturated aliphatic ethers, e.g. those set forth above, benzene methyl substituted benzene) at a temperature between −80° and +100° C.

Furthermore there can also be obtained such starting materials from a compound

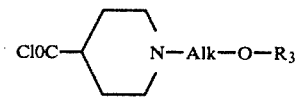

and the corresponding thiophene is the presence of $AlCl_3$ according to the Friedel-Crafts process.

Starting materials of formula V can be obtained for example through Friedel-Crafts acylation of a compound

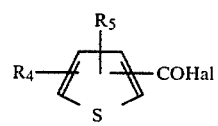

(Hal = Chlorine or Bromine)

with a compound

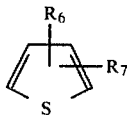

in the presence of AlCl₃ in a solvent such as dichloroethane, nitromethane at a temperature between 0° and 100° C.

Furthermore, they can be obtained through Grignard reaction of a compound

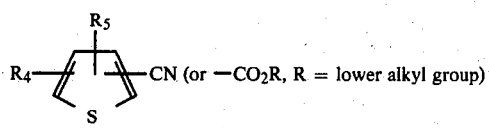

with a compound

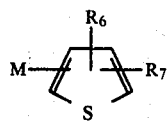

wherein M is lithium or—MgCl or—MgBr in a solvent or suspension agent such as is customary for Grignard reactions at a temperature between $-80°$ and $+100°$ C.

Starting materials of formula III wherein X is the group—MgHal can be obtained for example from compounds (of the formula III wherein X is chlorine, bromine or iodine through customary Grignard- or lithium-Grignard reaction using magnesium or metallic lithium in the customary solvents for this (for example tetrahydrofurane, lower aliphatic ethers, lower alkyl benzenes) at a temperature between 20°–120° C. In a given case the Grignard reaction must be initiated by means of iodine plus dibromoethane.

The compounds of the invention are generally obtains as racemates. The optically active antipodes are obtained either through the use of optically active starting materials or through the splitting of the racemate by way of the salts of optically active acids as for example: L-(+)-tartaric acid, D-(−)-tartaric acid, (+)-0,0′-dibenzoyl-D-tartaric acid, (−)-0,0′-dibenzoyl-L-tartaric acid, (−)-0, O′-dip-p-toluoyl-L-tartaric acid, (+)-0,0′dip-toluoyl-D-tartaric acid, (+)-camphor-10-sulfonic acid and others.

The compounds of general formula I can be converted into the salts by known methods. As anions for these salts there can be employed the known and therapeutically acceptable acid residues. Examples of such acids are sulfuric acid, phosphoric acid, hydrohalic acid, e.g. hydrochloric acid or hydrobromic acid, ethylenediamine tetraacetic acid, sulfamic acid, benzenesulfonic acid, p-toluenesulfonic acid, camphor sulfonic acid, methanesulfonic acid, guaiazulenesulfonic acid, maleic acid, fumaric acid, succinic acid, tartaric acid, lactic acid, ascorbic acid, glycolic acid, salicylic acid, acetic acid, propionic acid, gluconic acid, benzoic acid, citric acid, acetaminoacetic acid and hydroxyethane sulfonic acid.

The free bases can be produced again from the salts of the compounds in customary manner, for example by treating a solution in an organic medium, such as alcohols (e.g. methanol) with sodium carbonate or sodium hydroxide.

The conversion into the quaternary salts takes place by reaction of the corresponding secondary or tertiary amino compounds with lower alkyl halides (1 to 6 carbon atoms; chlorides, bromides, iodides, e.g. methyl chloride methyl bromide, methyl iodide, hexyl chloride, hexyl bromide, hexyl iodide, ethyl chloride, ethyl iodide, isopropyl bromide, butyl chloride, butyl bromide, butyl iodide) in a solvent or suspension agent such as aromatic hydrocarbons (e.g. benzene, toluene, xylene), halogenated aliphatic hydrocarbons (CHCl₃, CH₂Cl₂) saturated aliphatic ethers, e.g. diethyl ether, cyclic ethers (e.g. dioxane), dimethyl sulfate at a temperature between 0° and 100° C.

The compounds of the invention are suitable for the production of pharmaceutical compositions. The pharmaceutical compositions or medicaments can contain one or more of the compounds of the invention or even mixtures of them with other pharmaceutically active compounds. For the production of pharmaceutical preparations there can be used the usual pharmaceutical carriers and adjuvants.

As stated the compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers and diluents.

As carriers and assistants, for example, are those recommended in the following literature as adjuvants for pharmacy, cosmetic and related fields such as in Ullmann's Encyklopadie der technischen Chemie, Volume 4 (1953), pages 1 to 39; Journal of Pharmaceutical Sciences 52 (1963), pages 918 et seq., H.V. Dr. H. P. Fiedler, Lexicon der Hilfstoffe fur Pharmazie, Kosmetik und angrenzende Gebiete, Cantor kg. Aulendorf i. Württ. (1971).

Examples of such materials include gelatin, natural sugars such as sucrose or lactose, leithin, pectin, starch (for example cornstarch), alginic acid, tylose (methyl cellulose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil) mono-, di and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono-hydric aliphatic alcohols (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atoms, dimethyl acetamide, lactamide, lactates, e.g. ethyl lactate, ethyl carbonate, silicones (especially middle viscosity dimethyl polysiloxane), magnesium carbonate and the like.

For the production of solutions there can be used water of physiologically compatible organic solvents as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, paticularly between 10 and 20.

Such polyoxyethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metabisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester), benzoic acid, sodium benzoate, trichloroisobutyl alcohol, phenol, cresol, benzethonium chloride and formalin derivatives).

The pharmacological and galenical treatment of the compounds of the invention takes place according to the usual standard method. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonally, rectally, intravenously, nasally, vaginally, lingually, intravenously, intraarterially, intracardially, intramuscularly, intraperitoneally, subcutaneously or intracutaneously.

The addition of other medicines is also possible or favorable.

The compounds of the invention have good broncholytic-spasmolytic activity, a papaverine like activity, an antihistamine-antiserotonine activity as well as an antianaphylactic activity (asthma prophylatic activity).

These activities can be established for example through the following tests

Determination of the papavarine like activity: Method according to Magnus, see Pflügers Arch. Physiol. Vol. 102, page 103 (1904) as well as Pharmacological Experiments on isolated Preparation, 2nd edition, E. and S Livingstone, Edingburg and London 1970.

Determination of the bronchospasmolytic activity on the isolated tracheal spiral according to J. W. Constatine, see J. Pharm. Pharmakol Vol 17, pages 384 (1965), as well as in vivo on dogs and quinea pigs according to Konzett-Rüssler, Arch. Exper. Pathol. Pharmakol, Vol. 195, page 71 (1940).

Determination of the antihistamine-antiserotonine and asthma prophylactic activity through asthma experiments (histamine-spasm, acetylcholine-spasm serotonine-spasm, ovalbumin-spasm) on waking guinea pigs relying on Kallos and Pagel, Acta med Scand. Vol. 91, page 292 (1937), as well as according to the method of Niemegeers et al, Arch. Int. Pharmacodyn, Vol. 234, page 164 (1978).

For example in the above mentioned test method (brochospasmolytic experiment according to Konzett and Rüossler) at a dosage of 0.1 mg per kg of body weight in guines pigs the brochospasm given off by histamine on the average is completely suppressed.

This antihistaminic broncholytic activity is comparable with the activity of the known medicine Clemastin.

The lowest clearly bronchospasmolytically effective dosage in the above-stated animal tests, for example, is 0.1 mg/kg orally and 0.01 mg/kg intravenously.

As the general dosage range for the activity (animal experiments as above) there can be used, for example:

0.1 to 3 mg/kg orally, especially 1 mg/kg; 0.01 to 0.3 mg/kg intravenously, especially 0.1 mg/kg.

The compounds of the invention are indicated for: antiallergics (histamine-serotonine-antagonist), allergic reactions of the skin and mucous membranes, asthama prophylaxis.

The pharmaceutical preparations can contain for example between 1 and 10 mg of the active component or components of the invention.

The compounds can be delivered in the form of tablets, capsules, pills, dragees, plugs, salves, jellies, creams, dusts, aerosols or in liquid for, As liquid forms there can be used, for example oily or alcoholic or aqueous solutions as well as suspensions and emulsions. The preferred forms of use are tablets which for example contain between 2 and 10 mg or solutions which contain between 0.5 and 2% of active material.

In individual doses, the active components of the invention can be used for example in an amount of:

(a) in oral dispensation between 1 and 10 mg;
(b) in parenteral dispensation (for example, intravenously, intramuscularly) between 0.5 and 2 mg;
(c) in medicines for inhalation (solution or aerosols) between 0.3 and 1 mg.

For example, there is recommended the use of 1 to 3 tablets containing 2 to 20 mg of active ingredient 3 times daily or for example, intravenously the injection 1 to 3 times daily of a 1 to 10 ml ampoule containing 0.3 to 3 mg of active substance. In oral dispensation the minimum daily dosage for example is 5 mg; the maximum daily dosage in oral administration should not be over 200 mg.

In the treatment of dogs and cats, the individual oral dosages are for example approximately between about 0.5 and 2 mg/kg of body weight; the parenteral dosage between about 0.1 and 1 mg/kg body weight.

The acute toxicity of the compounds of the invention in the mouse (expressed by the $LD_{50}$ mg/kg method of Miller and Tainter, Proc. Soc. Exper. Biol. an Med. 57 (1944), pages 261 et seq.) in oral application is between 100 mg/kg and 500 mg/kg, and more than 500 mg/kg respectively.

The drugs can be used in human medicine, in veterinary medicine as well as in agriculture alone or in admixture with other pharmacologically active materials. The compounds can be used to treat dogs, cats, horses and cattle.

The methods can comprise, consist essentially of or consist of the steps set forth with materials shown. The compositions can comprise, consist essentially of or consist of the materials set forth.

Unless otherwise indicated all parts and percentages are by weight.

The present invention is illustrated by the following examples.

DESCRIPTION OF THE PREFERRED EMBODIMENTS

Example 1

4-(Di-3-thienyl-methylene)-N-(2-methoxy-ethyl)-piperidine

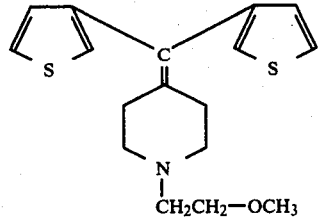

8.9 grams (0.034 mole) of 4-(di-3-thienyl-methylene)-piperidine and 18 grams (0.17 mole) of 2-chloroethyl-methyl ether were dissolves in 100 ml of xylene and heated under reflux for 10 hours in the presence of 22.4 grams of sodium carbonate. After the addition of water, separation of the organic phase, repeated extractions of the aqueous phase with chloroform, combination and drying of the organic phases the solvent was distilled off in a vacuum and the hydrochloride obtained using isopropanolic hydrochloric acid and acetone as solvents.

The recrystallization was carried out from acetone. M.P. of the hydrochloride 180° C.,
Yield: 30%

The thienyl starting material was obtained as follows

A solution of 122 grams (0.443 mole) of 4-(di-3-thienylmethylene)-N-methyl pyridine (produced according to process (b) of the above mentioned Engel U.S. application (Ser. No. 112,099) in 400 ml of toluene was dropped into a mixture of 100 grams (0.886 mole) of ethyl chloroformate and 200 ml of toluene at 80° C. After the end of the addition the reaction mixture was stirred for a further 3 hours at 80° C. and concentrated by distilling off the solvent in a vacuum. Hereby the 4-(di-3-thienyl-methylene)-N-carbethoxy-piperidine crystallized out and was recrystallized from isopropanol (Yield: 98%; M.P. 109°–111° C.).

A mixture of 163 grams (0.484 mole) of this carbethoxy compound, 120 grams (2.2 moles) of potassium hydroxide and 1200 ml of n-butanol were boiled under reflux until after thin layer chromatographic control the starting compound was completely reacted. The butanol was removed in a vacuum, the residue treated with water and shaken repeatedly with methylene chloride. The salt was formed with maleic acid employing acetone as the solvent. Yield: 68%; M.P. of the maleate 173° to 174° C.

The starting 4-(di-3-thienylmethylene)-N-methyl-piperidine starting material can be prepared as follows.

14 grams (0.048 mole) of (di-3-thienyl)-N-methyl-4-piperidyl)-carbinol (crude product) were dissolved in 200 ml of methanol, treated with 20 ml of 8 N isopropanolic hydrochloric acid and heated for 1 hour. The solvent was removed under reduced pressure and the hydrichloride obtained recrystallized from isopropanol. M.P. of the hydrochloride 230° C.; Yield 79%.

The starting carbinol was obtained in a manner analogous to Example 1(b) of the aforementioned Engel application Ser. No. 112,099.

In a manner analogous to Example 1 there were produced the compounds of the following formula:

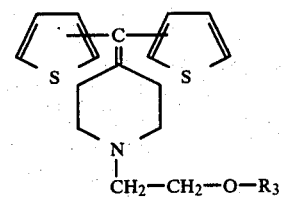

In each case there was reacted 0.034 mole of the corresponding 4-(dithienyl-methylene)-pyridine with 0.17 mole of the compound Cl—CH₂—CH₂—OR₃. The hydrochloride of the end product obtained in each case was recrystallized from isopropanol.

TABLE 1

| Ex. | Position of the Two Thienyl Groups | R₃ | Yield | M.P. of the Hydrochloride |
|---|---|---|---|---|
| 2 | 3-position | —(CH₂)₂—OH | 31% | 178° C. |
| 3 | 3-position | —(CH₂)₂—O—(CH₂)₂—OH | 46% | 128° C. |
| 4* | 2-position | —CH₃ | 18% | 169–170° C. |

TABLE 1-continued

| Ex. | Position of the Two Thienyl Groups | $R_3$ | Yield | M.P. of the Hydrochloride |
|---|---|---|---|---|
| 5 | 2-position | —(CH$_2$)$_2$—OH | 20% | 145° C. |

*In this example before the formation of the salt there was carried out a chromatographic column purification on silica gel (elution agent: Chloroform/Methanol 98%: 20% by volume).

Example 6

4-(Di-2-thienyl-methylene)-N-(2-cyclopentyloxyethyl)-piperidine

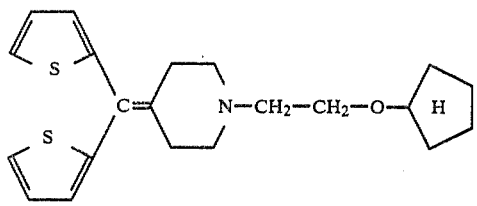

6 grams (0.0175 mole) of 4-(di-2-thienyl-methylene)-N-(2-hydroxyethyl)-piperidine hydrochloride were added in portions to a suspension of 1.3 grams of NaH (80%) in 100 ml of dry xylene. The mixture was heated to boiling until the evolution of hydrogen stopped. At the boiling heat there were dropped in 5.3 grams of cyclopentyl bromide dissolved in 10 ml of xylene. After 16 hours reaction time the product was hydrolyzed in the cold with water, the xylene phase separated off, dry and concentrated. The product was purified by chromatography using silica gel for the dry column chromatography employing ethyl acetate as elution agent and the oxalate precipitated from acetone solution. M.P. of the oxalate 193°–195° C.; Yield 32%.

EXAMPLES OF PHARMACEUTICAL PREPARATIONS

Example 7

Tablets 1 kg of active material (the compound of Example 2 was mixed with 5 kg of lactose and 3 kg of microcrystalline cellulose and granulated with a solution of 0.3 kg of polyvinyl pyrrolidone in 1.2 kg of water in known manner.

After mixing in 3.45 kg of microcrystalline cellulose, 2 kg of corn starch, 0.05 kg of highly dispersed silica as well as 0.2 kg of magnesium stearate there were pressed tablets weighting 150 mg and having a diameter of 7 mm and a radius of curvature of 5 mm. The hardness of the tablets was 4–7 kg (Heberlein Hardness Tester). Each tablet contained 10 mg of active material.

Example 8

Ampoules 10 grams of active material (compound of Example 2) together with 88.5 grams of sodium chloride were dissolved in 9 liters of water suitable for purpose of injection, the solution filled up to 10 liters with water suitable for injection purposes and filtered. After filling the solution into ampoules to 1 ml sterilization was carried out in the customary manner at 120° C. over 20 minutes. Each ampoule contained 1 mg of active material in 1 ml.

The entire disclosure of British priority application 7901660 is hereby incorporated by reference. A certified copy of this British Application is in the record of the instant case and was filed along with the original application papers.

What is claimed is:

1. A compound having the formula

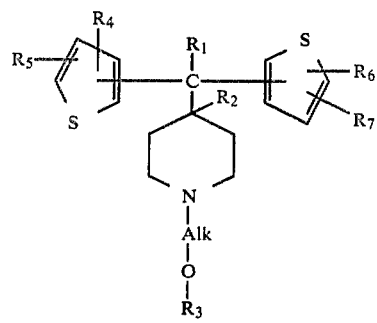

where $R_1$ is hydrogen or hydroxy, $R_2$ is hydrogen or $R_1$ and $R_2$ together represent a second bond between the carbon atoms carrying $R_1$ and $R_2$, Alk is a $C_2$–$C_6$ alkylene group, $R_3$ is a $C_3$–$C_8$-cycloalkyl group, a $C_1$–$C_6$-alkyl group, a $C_1$–$C_6$-hydroxyalkyl group or a $C_2$–$C_6$-hydroxyalkoxy-$C_1$–$C_6$-alkyl group and the groups $R_4$, $R_5$, $R_6$ and $R_7$ are the same or different and are hydrogen, $C_1$–$C_6$-alkyl group or halogen atoms, an N-oxide thereof, a lower alkyl quarternary salt thereof or an acid addition salt thereof with a therapeutically acceptable acid.

2. A compound according to claim 1 where both thienyl groups are joined in the two position to the adjacent carbon atom.

3. A compound according to claim 1 where both thienyl groups are joined in the three position to the adjacent carbon atom.

4. A compound according to claim 1 wherein $R_1$ and $R_2$ together represent a second bond between the carbon atoms carrying $R_1$ and $R_2$.

5. A compound according to claim 4 where $R_3$ is a $C_1$–$C_6$-alkyl group.

6. A compound according to claim 5 where $R_3$ is methyl.

7. A compound according to claim 4 where $R_3$ is a $C_1$–$C_6$-hydroxyalkyl group.

8. A compound according to claim 7 where $R_3$ is hydroxyethyl.

9. A compound according to claim 4 where $R_3$ is $C_2$–$C_6$-hydroxyalkoxy-alkyl.

10. A compound according to claim 9 where $R_3$ is hydroxyethoxyethyl.

11. A compound according to claim 4 where $R_3$ is a $C_3$–$C_8$ cycloalkyl group.

12. A compound according to claim 11 where $R_3$ is cyclopentyl.

13. A compound according to claim 1 where Alk is the ethylene group.

14. A compound according to claim 1 in the form of the quaternary salts.

15. A compound according to claim 14 wherein the quaternary salt is a salt with a compound of the formula $R_8Y$ where $R_8$ is alkyl of 1 to 20 carbon atoms and Y is chlorine, bromine or iodine.

16. A compound according to claim 1 which is an N-oxide.

17. A medicament suitable for use in relieving bronchospasm, relieving an anaphylactic attack or to have an antihistamine effect which comprises a compound as claimed in claim 1 in an amount effective for such purpose together with a pharmacologically acceptable carrier.

18. A method of relieving bronchospasm in a mammal comprising administering to the mammal an effective amount of a compound of claim 1 to relieve the bronchospasm.

19. A method according to claim 18 wherein the compound is administered orally.

20. A method according to claim 18 wherein the compound is administered intravenously.

21. A method according to claim 18 wherein $R_1$ and $R_2$ together represent a second bond between the carbon atoms carrying $R_1$ and $R_2$.

22. A method according to claim 21 where Alk is the ethylene group, $R_3$ is cyclopentyl, methyl, hydroxyethyl or hydroxyethoxyethyl and $R_4$, $R_5$, $R_6$ and $R_7$ are hydrogen.

23. A method of relieving an anaphylactic attack in a mammal comprising administering to the mammal an effective amount of a compound of claim 1 to have an antianaphylactic action.

24. A method according to claim 23 wherein $R_1$ and $R_2$ together represent a second bond between the carbon atoms carrying $R_1$ and $R_2$.

25. A method according to claim 24 where Alk is the ethylene group, $R_3$ is cyclopentyl, methyl, hydroxyethyl or hydroxyethoxyethyl and $R_4$, $R_5$, $R_6$ and $R_7$ are all hydrogen.

26. A method of relieving histamine caused attack in a mammal comprising administering to the mammal an effective amount of a compound of claim 1 to have an antihistamine effect.

27. A method according to claim 26 wherein $R_1$ and $R_2$ together represent a second bond between the carbon atoms carrying $R_1$ and $R_2$.

28. A method according to claim 27 where Alk is the ethylene group, $R_3$ is cyclopentyl, methyl, hydroxyethyl or hydroxyethoxyethyl and $R_4$, $R_5$, $R_6$ and $R_7$ are all hydrogen.

29. A compound according to claim 1 which is either in its free base form or in the form of an acid addition salt thereof with a therapeutically acceptable acid.

30. A compound according to claim 29 which is in its free base form.

* * * * *